United States Patent [19]

Jautelat et al.

[11] Patent Number: 4,936,907
[45] Date of Patent: Jun. 26, 1990

[54] PLANT GROWTH-REGULATING AZOLYL SPIRO COMPOUNDS

[75] Inventors: Manfred Jautelat, Burscheid; Hans-Ludwig Elbe, Wuppertal; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 263,101

[22] Filed: Oct. 26, 1988

[30] Foreign Application Priority Data

Nov. 3, 1987 [DE] Fed. Rep. of Germany ....... 3737170

[51] Int. Cl.$^5$ .................. C07D 405/14; A01N 43/653
[52] U.S. Cl. ......................................... 71/92; 548/101; 548/266.4; 71/76
[58] Field of Search ...................... 71/92, 76; 548/262, 548/101

[56] References Cited

FOREIGN PATENT DOCUMENTS 0023756 2/1981 European Pat. Off. .
0142684 5/1985 European Pat. Off. .

*Primary Examiner*—Glennon H. Hollrah
*Assistant Examiner*—Patricia L. Morris
*Attorney, Agent, or Firm*—Sprung Horn Kramer & Woods

[57] ABSTRACT

Plant growth-regulating azolyl spiro compounds of the formula

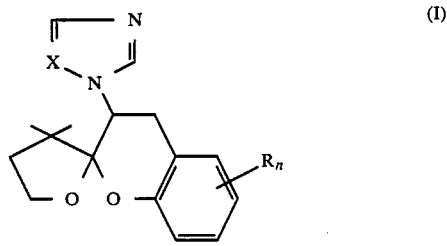

in which
R stands for halogen, alkyl, alkoxy, alkylthio, optionally substituted phenyl, optionally substituted phenoxy, amino, alkylamino and/or dialkylamino,
n stands for the numbers 0, 1, 2 or 3 and
X stands for nitrogen or a CH group, and addition products thereof with acids and metal salts.

10 Claims, No Drawings

PLANT GROWTH-REGULATING AZOLYL SPIRO COMPOUNDS

The present invention relates to new azolyl spiro compounds, a process for their preparation and their use as plant growth regulators.

It has already been disclosed that certain azolyl derivatives possess plant growth-regulating properties. In general, the activity of these substances is good; however, the plant growth-regulating activity is not always sufficient when they are employed at low application rates.

New azolyl spiro compounds of the formula

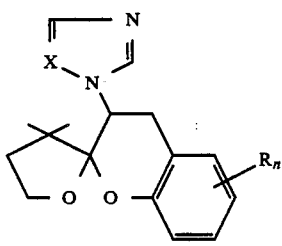

(I)

in which
R stands for halogen, alkyl, alkoxy, alkylthio, optionally substituted phenyl, optionally substituted phenoxy, amino, alkylamino and/or dialkylamino,
n stands for the numbers 0, 1, 2 or 3 and
X stands for nitrogen or a CH group,
and acid addition salts and metal salt complexes thereof have now been found.

Depending on the position of the azolyl radical relative to the plan of the tetrahydrofuran ring, the substances according to the invention can be obtained in an E form and a Z form, "E" standing for "entgegen" [opposed] and "Z" standing for "zusammen" [together]. The Z form can be described by the formula

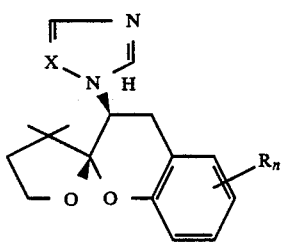

(I-Z)

whereas the E form can be described by the formula

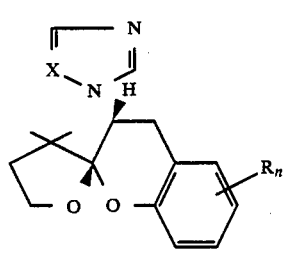

(I-E)

The invention relates both to the individual E and Z forms and to mixtures thereof.

Furthermore, it has been found that azolyl spiro compounds of the formula (I) and acid addition salts and metal salt complexes thereof are obtained when azolyl vinyl compounds of the formula

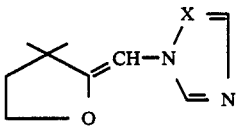

(II)

in which
X has the abovementioned meaning are reacted with phenols of the formula

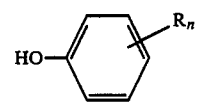

(III)

in which
R and n have the abovementioned meaning, in the presence of a catalyst and, if appropriate, in the presence of a diluent, and the resulting tetrahydrofuran derivatives of the formula

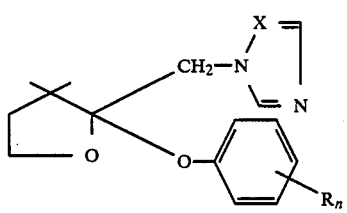

(IV)

in which
R, X and n have the abovementioned meaning, are reacted with formaldehyde in the presence of a catalyst and, if appropriate, in the presence of a diluent, and then, if appropriate, compounds of the formula (I) thus obtained are subjected to an addition reaction with an acid or a metal salt.

Finally, it has been found that the new azolyl spiro compounds of the formula (I) and acid addition salts and metal salt complexes thereof possess pronounced plant growth-regulating properties.

Surprisingly, the substances according to the invention show a better plant growth-regulating activity than the constitutionally most similar disclosed compounds of the same type of action.

Formula (I) provides a general definition of the azolyl spiro compounds according to the invention. In this formula,
R preferably stands for fluorine, chlorine, bromine, iodine, alkyl having 1 to 4 carbon atoms, alkoxy having 1 to 4 carbon atoms, alkylthio having 1 to 4 carbon atoms, phenyl which is optionally substituted by halogen and/or alkyl having 1 to 4 carbon atoms, phenoxy which is optionally substituted by halogen and/or alkyl having 1 to 4 carbon atoms, amino, alkylamino having 1 to 4 carbon atoms and/or dialkylamino having 1 to 4 carbon atoms in each alkyl group,
n preferably stands for the numbers 0, 1, 2 or 3 and
X preferably stands for nitrogen or a CH group.

If n stands for 2 or 3, the radicals standing for R can be identical or different from one another.

Compounds of the formula (I) in which

R stands for fluorine, chlorine, bromine, iodine, methyl, ethyl, n-propyl, iso-propyl, n-butyl sec.-butyl, isobutyl, tert.-butyl, methoxy, ethoxy, methylthio, ethylthio, phenyl which is optionally monosubstituted or disubstituted by identical or different substituents from the series comprising fluorine, chlorine, bromine and/or methyl, for phenoxy which is optionally monosubstituted or disubstituted by identical or different substituents from the series comprising fluorine, chlorine, bromine and/or methyl, for amino, methylamino, ethylamino, dimethylamino and/or diethylamino, n stands for the numbers 0, 1 or 2 and X stands for nitrogen or a CH group, are particularly preferred.

Other preferred compounds according to the invention are addition products of acids and those azolyl spiro compounds of the formula (I) in which R, X and n have the meanings which have already been mentioned as being preferred for the radicals or this index.

Suitable acids for addition are preferably hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Additionally preferred compounds according to the invention are addition products of salts of metals of main groups II to IV and of sub-groups I, II and IV to VIII of the Periodic Table of the Elements and of those azolyl spiro compounds of the formula (I) in which R, X and n have the meanings which have already been mentioned as being preferred for these radicals or this index.

Among these, particularly preferred salts are those of copper, zinc, manganese, magnesium, tin, iron and of nickel. Suitable anions of these salts are those which are derived from those acids which lead to physiologically acceptable addition products.

In this context, particularly preferred acids of this type are the hydrohalic acids, such as, for example, hydrochloric acid and hydrobromic acid, furthermore phosphoric acid, nitric acid and sulphuric acid.

Examples of azolyl spiro compounds of the formula (I) which may be mentioned are the substances listed in the table below.

TABLE 1

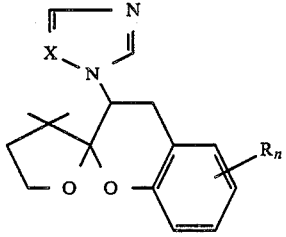

(I)

| $R_n$ | X | $R_n$ | X |
|---|---|---|---|
| 4-Cl | CH |  4-O—⟨phenyl⟩—Cl | CH |
| 4-Cl, 6-CH₃ | CH | 4-NH₂ | N |
| 4-F | CH | 4-NH₂ | CH |
| 4,6-Cl₂ | CH | 4-NHCH₃ | N |
| 4-OCH₃ | CH | 4-NHCH₃ | CH |
| 4-SCH₃ | N | 4-N(CH₃)₂ | N |
| 4-CH₃ | N | 4-N(CH₃)₂ | CH |
| 4,6-(CH₃)₂ | N | | |
| 4—⟨phenyl⟩ | N | | |
| 4—⟨phenyl⟩ | CH | | |
| 4—⟨phenyl-Cl⟩ | N | | |
| 4—⟨phenyl-Cl⟩ | CH | | |
| 4-O—⟨phenyl⟩ | N | | |
| 4-O—⟨phenyl⟩ | CH | | |
| 4-O—⟨phenyl-Cl⟩ | N | | |

If (3,3-dimethyl-tetrahydrofuran-2-ylidene)(1,2,4-triazol-1-yl)-methane and 4-chlorophenol are used as starting substances and paraformaldehyde is used as the reaction component, the course of the process according to the invention can be illustrated by the following equation:

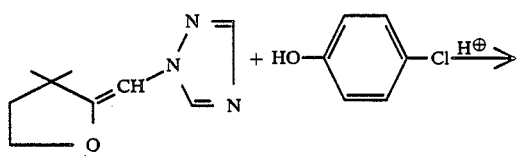

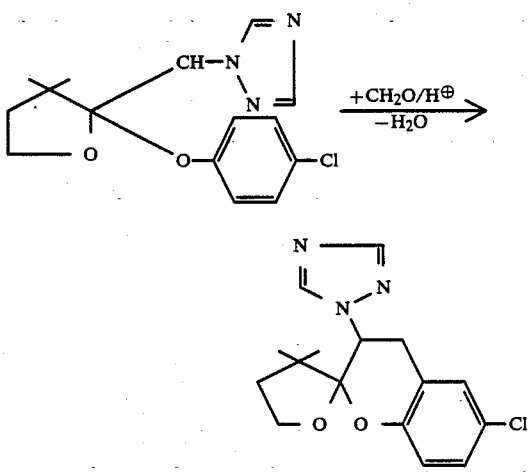

Formula (II) provides a definition for the azolyl vinyl compounds required as starting substances in the process according to the invention. In this formula, X stands for nitrogen or a CH group.

The azolyl vinyl compounds of the formula (II) have already been disclosed (cf. EP-OS No. 0,203,504).

Formula (III) provides a general definition for the phenols furthermore required as starting products in the process according to the invention. In this formula, R and n preferably have those meanings which have already been mentioned in connection with the description of the substances of the formula (I) according to the invention as being preferred for this radical or this index.

The phenols of the formula (III) are known or can be prepared by methods known in principle.

The tetrahydrofuran derivatives of the formula (IV) obtained as intermediates while carrying out the process according to the invention are new.

When carrying out the process according to the invention, formaldehyde is used as a reaction component. It can be employed in the trimeric form as trioxane or in polymeric form as paraformaldehyde.

Suitable catalysts for carrying out the process according to the invention are all acid reaction accelerants customary for such reactions, both in the first and in the second stage. Preferably, strong inorganic and organic acids, such as hydrochloric acid, trifluoroacetic acid and toluenesulphonic acid may be used.

The process according to the invention is carried out either in the absence of additional diluents or in the presence of inert solvents, both in the first and in the second stage. Preferably suitable for this purpose are inert organic solvents, for example ethers, such as tetrahydrofuran and dioxane, furthermore esters such as butyl acetate, moreover acids, such as acetic acid or propionic acid, and also nitriles, such as acetonitrile and propionitrile.

In the process according to the invention, the reaction temperatures may be varied within a relatively wide range, when carrying out both the first and the second stage. In general, each of the processes is carried out at temperatures between 50° C. and 150° C., preferably between 60° C. and 120° C.

The process according to the invention is generally carried out under atmospheric pressure. However, it is also possible for the process to be carried out under elevated or reduced pressure.

When carrying out the process according to the invention, 1 to 2 moles preferably 1 to 1.5 moles of phenol of the formula (III) and 1 to 4 moles, preferably 1.5 to 2.5 moles, of formaldehyde and furthermore 0.1 to 1.5 moles of catalyst are generally employed per mol of azolyl vinyl compounds of the formula (II). Working up is carried out by customary methods.

The process according to the invention can be carried out in a manner such that, initially, the tetrahydrofuran derivative of the formula (IV) is prepared, which is then reacted to the final product in a separate step. However, it is also possible to carry out the process as a one-pot reaction.

In the preparation, the azolyl spiro compounds according to the invention are generally obtained in the form of mixtures of E/Z isomers. These mixtures can be separated by customary methods, e.g. by means of chromatography, to give the individual components.

The $^1H$ nuclear resonance spectra of the E and Z forms of the azolyl spiro compounds of the formula (I) exhibit characteristic differences. In the case of the Z forms, the coupling constant of the H atom on the carbon atom carrying the azolyl radical with the two hydrogen atoms of the adjacent $CH_2$ group in the six-membered ring is at approximately 7 to 9 Hz, while the equivalent hydrogen atom of the E forms has a coupling constant of approximately 6 Hz.

The azolyl spiro compounds of the formula (I) obtainable by the process according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, e.g. by dissolving a compound of the formula (I) in a suitable inert solvent and adding the acid, e.g. hydrochloric acid, and they can be isolated in a known manner, e.g. by filtration, and if appropriate can be purified by washing with an inert organic solvent.

Suitable salts for the preparation of metal salt complexes of the compounds of the formula (I) are preferably those salts of metals which have already been mentioned in connection with the description of the metal salt complexes according to the invention as being preferred metal salts.

The metal salt complexes of the compounds of the formula (I) can be obtained in a simple manner by customary methods, such as, e.g. by dissolving the metal salt in alcohol, for example ethanol, and adding the solution to compounds of the formula (I). Metal salt complexes can be isolated in a customary manner, e.g. by filtration, and, if appropriate, can be purified by recrystallization.

The active compounds according to the invention engage in the metabolism of plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention are preferably suitable for inhibiting plant growth. They can be used particularly advantageously for inhibiting growth of dicotyledon plants, such as rape, soy beans and cotton.

The active compounds according to the invention also exhibit fungicidal activity. They can be used particularly advantageously against fungal attack in cereals and for combating Botrytis.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts applied can be varied within a substantial range. In general, 0.01 to 50 kg, preferably 0.05 to 10 kg, of active compound are used per hectare of soil surface.

As regards the time of application, the rule is that growth regulators are applied within a preferred period of time, the exact definition of which depends on the climatic and vegetative circumstances.

Preparation and use of the active compounds according to the invention can be seen from the following examples.

PREPARATION EXAMPLES

EXAMPLE 1

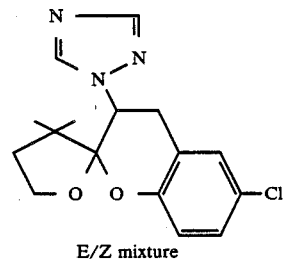

(I-1)

E/Z mixture

A mixture consisting of 9.0 g (0.05 mole) of (3,3-dimethyltetrahydrofuran-2-ylidene)-(1,2,4-triazol-1-yl)-methane, 6.4 g (0.05 mole) of 4-chlorophenol, 3.0 g (0.1 mole) of paraformaldehyde and 1 ml of trifluoroacetic acid is heated at 100° C. for 22 hours. A further 1.5 g (0.05 mole) of paraformaldehyde are then added, and the mixture is heated at 100° C. for a further 20 hours. After cooling to room temperature, the reaction mixture is diluted with dichloromethane and shaken out with 2N aqueous sodium hydroxide solution several times. The organic phase is separated off, dried and concentrated by stripping off the solvent under reduced pressure. In this manner, 13.2 g (82% of theory) of the spiro compound denoted above are obtained in the form of a mixture E:Z=1.9:1.

Melting range: 125°–150° C.

Preparation of the starting product

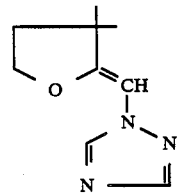

85 g (1.23 moles) of 1,2,4-triazole and 464 g (33.6 moles) of potassium carbonate are introduced into 2.5 l of acetone. 220 g (1.12 moles) of 1,5-dichloro-3,3-dimethyl-2-pentanone are added dropwise at room temperature and without cooling. When the addition is complete, the mixture is stirred for a further 2 hours at reflux temperature.

The reaction mixture is cooled, filtered off by suction, and the mother liquor is evaporated under reduced pressure. The residue is taken up in dichloromethane. The solution is washed with water, dried with sodium sulphate and evaporated. The residue remaining is stirred with petroleum ether, removed by suction and dried at 50° C. in vacuo.

145.3 g (56.5% of theory) of (3,3-dimethyl-tetrahydrofuran-2-ylidene)-(1,2,4-triazol-1-yl)-methane of melting point 47° C. are obtained.

EXAMPLES 2 AND 3

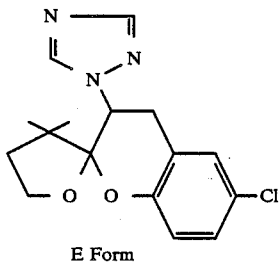

E Form (I-2)

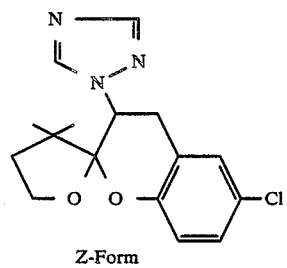

Z-Form (I-3)

By chromatography on silica gel, the E/Z mixture (I-1) is separated into the individual isomers, ethyl acetate being used as the eluent. In this process, the following components are obtained:

1. E isomer of the formula (I-2)
Melting point: 132°–134° C.
$^1$H-NMR (CDCl$_3$)δ: 0.56 (s, 3 H), 1.25 (s, 3 H), 1.75 (m, 1 H), 2.35 (m, 1 H), 2.84 (d, J=17.5 Hz, 1 H), 3.65 (2 d, J=17.5 and 6 Hz, 1 H), 3.95 (m, 2 H), 5.14 (d, J=6 Hz, 1 H), 6.92 (d, J=8.5 Hz, 1 H), 7.12 (d, J=2 Hz, 1 H), 7.22 (2d, J=2 and 8.5 Hz, 1 H), 8.0 (s, 1 H), 8.05 (s, 1 H).

2. Z isomer of the formula (I-3)
Melting point: 170°–173° C.
$^1$H-NMR (CDCl$_3$)δ: 0.8 (s, 1 H), 1.15 (s, 1 H), 1.75 (m, 1 H), 2.4 (m, 1 H), 3.3 (d, J=7 Hz, 1 H), 3.35 (d, J=9 Hz, 1 H), 4.1 (m, 2 H); 5.0 (2 d, J=7 and 9 Hz, 1 H), 6.8 (d, J=8.5, 1 H), 7.2 (d, J=3.5 Hz, 1 H); 7.15 (2 d, J=3.5 and 8.5 Hz, 1 H), 8.1 (s, 1 H), 8.7 (s, 1 H).

EXAMPLE 4

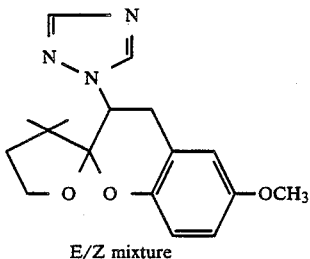

E/Z mixture (I-4)

A mixture consisting of 3.6 g (20 mmol) of (3,3-dimethyl-tetrahydrofuran-2-ylidene)-(1,2,4-triazol-1-yl)methane, 2.5 g (20 mmol) of 4-methoxyphenol, 0.6 g (20 mmol) of paraformaldehyde, 1 ml of trifluoroacetic acid and 50 ml of dioxane is refluxed for 192 hours, while adding 1.2 g (40 mmol) of paraformaldehyde every 24 hours, in portions of 0.2 g. After cooling to room temperature, the reaction mixture is diluted with dichloromethane and shaken several times with 2N aqueous sodium hydroxide solution. The organic phase is separated off, dried and concentrated by stripping off the solvent under reduced pressure. 5.4 g of a product which is filtered with ethyl acetate over 50 g of silica gel for further purification are obtained. After the solvent has been stripped off, 4.5 g (72.5% of theory) of the spiro compound denoted above remain in the form of a mixture E:Z=0.5:1, with a melting point of 127°–130° C.

Following the methods indicated in Examples 1 and 3, the substances whose formulae are listed in the following Table 2 can also be prepared.

TABLE 2

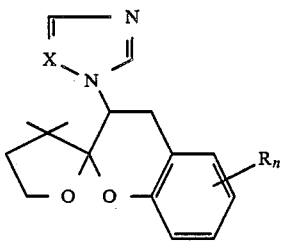

(I)

| Example No. | Compound | R$_n$ | X | E:Z ratio |
|---|---|---|---|---|
| 5 | I-5 | 4-Cl, 6-CH$_3$ | N | 0.32:1 |
| 6 | I-6 | 4-F | N | 2.6:1 |
| 7 | I-7 | 4,6-Cl$_2$ | N | 0.22:1 |

The E/Z mixtures listed in Examples 5–7 are obtained in the form of oily substances which were characterized unambiguously by their $^1$H-NMR spectra.

EXAMPLE A

Growth of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 2 weeks, the additional growth of the plants is measured and growth is calculated in per cent of the growth of the control plants. 100% growth means that growth corresponds to that of the control plants and 0% means that growth has stopped.

In this test, the active compounds according to the invention described in Examples (1) and (5) show a very pronounced inhibition of growth.

EXAMPLE B

Growth of soya beans

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. In this stage, the plants are sprayed with the preparations of active compound until dripping wet. After 2 weeks, the additional growth is measured on all the plants and growth is calculated in per cent of the growth of the control plants. 100% growth means that growth corresponds to that of the control plants and 0% means that growth has stopped. Values higher than 100% characterize increase of growth.

In this test, the substances according to the invention described in Examples (1), (5) and (6) show a very pronounced growth-inhibiting action.

EXAMPLE C

Growth of oilseed rape

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Oilseed rape plants are grown in a greenhouse until the 5th leaf has emerged. In this stage, the plants are sprayed with the preparations of active compound until dripping wet. After 2 weeks, the additional growth of the plants is measured, and growth is calculated in per cent of the growth of the control plants. 100% growth means that growth corresponds to that of the control plants, and 0% means that growth has stopped. Values higher than 100% denote increased growth.

In this test, the active compound according to the invention described in Example (1) shows very pronounced growth-inhibiting action.

EXAMPLE D

Growth of corn

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Corn plants are grown in the greenhouse until they have reached the two-leaf stage. In this stage, the plants are sprayed with the preparations of active compound until dripping wet. After two weeks, additional growth is measured on all the plants and growth is calculated in per cent of the additional growth of the control plants. 100% growth means that growth corresponds to the control plants, and 0% means that growth has stopped. Values higher than 100% denote increased growth.

In this test, the active compound according to the invention described in Example (1) exhibits very pronounced growth-inhibiting action.

It will be appreciated that the instant specification and claims are set forth by way of illustration and not limitation, and that various modifications and changes may be made without departing from the spirit and scope of the present invention.

What is claimed is:

1. An azolyl spiro compound of the formula

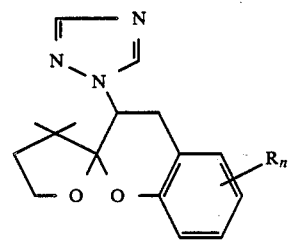

in which
R stands for fluorine, chlorine, bromine, iodine, alkyl having 1 to 4 carbon atoms, alkoxy having 1 to 4 carbon atoms, alkylthio having 1 to 4 carbon atoms, phenyl which is optionally substituted by halogen or alkyl having 1 to 4 carbon atoms, phenoxy which is optionally substituted by halogen or alkyl having 1 to 4 carbon atoms, amino, alkylamino having 1 to 4 carbon atoms or dialkylamino having 1 to 4 carbon atoms in each alkyl group, and
n stands for the numbers 0, 1, 2 or 3, or an addition product thereof with an acid or metal salt.

2. An azolyl spiro compound or addition product according to claim 1, in which
R stands for fluorine, chlorine, bromine, iodine, methyl, ethyl, n-propyl, isopropyl, n-butyl, sec.-butyl, iso-butyl, tert.-butyl, methoxy, ethoxy, methylthio, ethylthio, phenyl which is optionally monosubstituted or disubstituted by identical or different substituents from the group consisting of fluorine, chlorine, bromine and methyl, for phenoxy which is optionally monosubstituted or disubstituted by identical or different substituents from the group consisting of fluorine, chlorine, bromine and methyl, for amino, methylamino, ethylamino, dimethylamino or diethylamino, and
n stands for the numbers 0, 1 or 2.

3. A compound according to claim 1, wherein such compound is

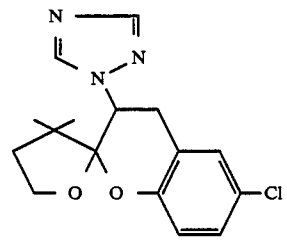

or an addition product thereof with an acid or metal salt.

4. A compound according to claim 1, wherein such compound is

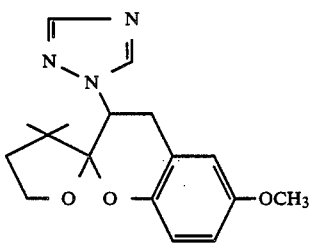

or an addition product thereof with an acid or metal salt.

5. A compound according to claim 1, wherein such compound is

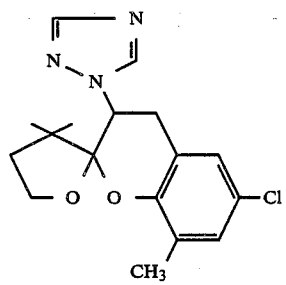

or an addition product thereof with an acid or metal salt.

6. A compound according to claim 1, wherein such compound is

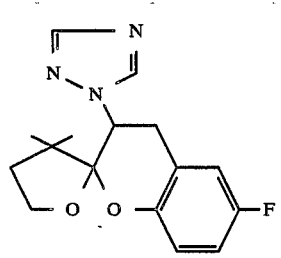

or an addition product thereof with an acid or metal salt.

7. A compound according to claim 1, wherein such compound is

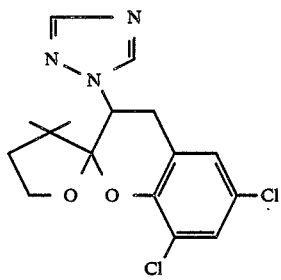

or an addition product thereof with an acid or metal salt.

8. A plant growth-regulating composition comprising a plant growth-regulating effective amount of a compound or addition product according to claim 1 and an inert diluent.

9. A method of regulating the growth of plants which comprises applying to such plants or to a locus in which said plants are growing or are to be grown a plant growth-regulating effective amount of a compound or addition product according to claim 1.

10. The method according to claim 9, wherein such compound is

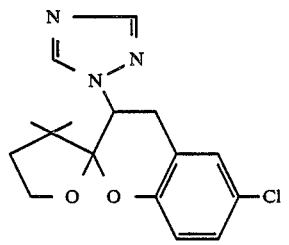

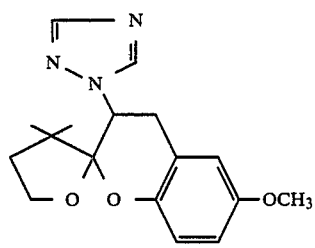

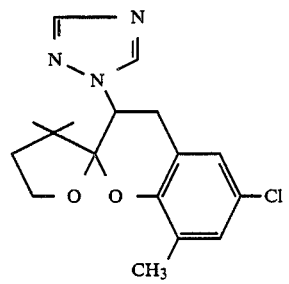

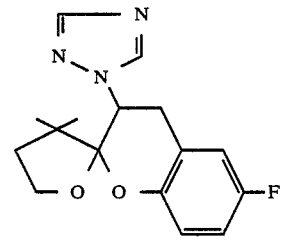

or

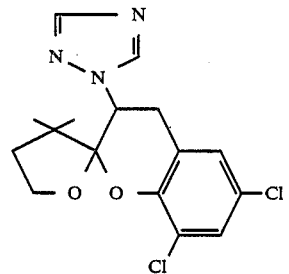

or an addition product thereof with an acid or metal salt.

* * * * *